US00PP15489P2

(12) United States Plant Patent
Speichert

(10) Patent No.: US PP15,489 P2
(45) Date of Patent: Jan. 25, 2005

(54) ***ARUNDO* PLANT NAMED 'ORIENTAL GOLD'**

(50) Latin Name: *Arundo formosana*
Varietal Denomination: Oriental Gold

(76) Inventor: C. Greg Speichert, P.O. Box 154, St. John, IN (US) 46373

( * ) Notice: Subject to any disclaimer, the term of this patent is extended or adjusted under 35 U.S.C. 154(b) by 66 days.

(21) Appl. No.: 10/809,209

(22) Filed: Mar. 25, 2004

(51) Int. Cl.[7] ..... A01H 5/00
(52) U.S. Cl. ..... Plt./384
(58) Field of Search ..... Plt./384

*Primary Examiner*—Anne Marie Grunberg
*Assistant Examiner*—Annette H Para
(74) *Attorney, Agent, or Firm*—Penny J. Aguirre

(57) ABSTRACT

*Arundo formosana* 'Oriental Gold', is a new and unique cultivar that is characterized by its variegated foliage of yellow-green to creamy yellow with green stripes, its clump-forming, bushy habit and usefulness in container plantings .

2 Drawing Sheets

Botanical classification: *Arundo formosana.*
Varietal designation: 'Oriental Gold'.

BACKGROUND OF THE INVENTION

The present invention relates to a new and distinct cultivar of *Arundo formosana* and will be referred to hereafter by its cultivar name, 'Oriental Gold'. 'Oriental Gold' represents a new cultivar of Tiawan grass, an ornamental grass grown for landscape use.

The inventor discovered and selected the new cultivar, 'Oriental Gold', in a cultivated garden in Cedar Lake, Ind. in 1994. 'Oriental Gold' was discovered as a naturally occurring cane sport of *Arundo formosana*. Initially, a small cane sport was discovered that was green with a small yellow stripe and subsequent cane cuttings were performed and re-selected until the new cultivar was selected with foliage that was consistently variegated with foliage that was predominately yellow-green to creamy yellow in color with deeper colored green stripes. The leaf variegation pattern of 'Oriental Gold' is unique and unlike any other known cultivars of *Arundo formosana* known to the inventor.

Asexual reproduction of the new cultivar was first accomplished by cane cuttings in Cedar Lake, Ind. in 1995 by the inventor. The characteristics of this cultivar have been determined to be stable and are reproduced true to type in successive generations.

SUMMARY OF THE INVENTION

The following traits have been repeatedly observed and represent the characteristics of the new cultivar. The new *Arundo* has not been observed under all possible environmental conditions. The phenotype may vary somewhat with variations in temperature, day-length, light intensity, soil types, and water and fertility levels without, however, any variance in genotype. The measurements, observations, and descriptions that follow describe plants grown outdoors for two years from a single cane division in Cedar Lake, Ind. These attributes in combination distinguish 'Oriental Gold' from any selections of *Arundo* known to the inventor.

1. The foliage of 'Oriental Gold' is variegated with yellow-green to creamy yellow foliage with green stripes. Horticulturally, 'Oriental Gold' would be considered to have gold and green variegated foliage.
2. The growth habit of 'Oriental Gold' is clump-forming with a fountain-shaped bushy appearance similar to Bamboo but is less invasive than Bamboos and *Arundo donax*; a taller, more robust species.
3. 'Oriental Gold' reaches about 1.8 to 2 m (6 to 7 ft) in height with a spread of 1.8 to 2.7 m (6 to 9 ft) in 3 years when planted from a one gallon container.
4. The clump-forming growth habit, bushy habit, and cascading foliage making it useful for container use.
5. Blooms in late fall or winter in response to short days with inflorescences composed of panicles of slender, airy racemes.

BRIEF DESCRIPTION OF THE DRAWING

The accompanying colored photographs illustrate the overall appearance and distinct characteristics of the new *Arundo.* The plants used for the photographs are 1 year-old plants as grown in two-gallon containers from 5 cm cane divisions of 'Oriental Gold'.

The photograph in FIG. One illustrates the branching habit of 'Oriental Gold' in early fall.

The photograph in FIG. Two is a close-up view of the foliage and depicts the growth habit in early summer.

FIG. Three is photograph of the inflorescence in late winter under greenhouse conditions.

The colors in the photographs are as close as possible with the digital photography techniques available, the color values cited in the detailed botanical description accurately describe the colors of the new *Arundo.*

BOTANICAL DESCRIPTION OF THE PLANT

The following is a detailed description of the new cultivar as grown in an outdoor trial bed for two years from a cane division in Cedar Lake, Ind. The color determination is in accordance with the 2001 R.H.S. Colour Chart of The Royal Horticultural Society, London, England, except where general color terms of ordinary dictionary significance are used.

Botanical classification: 'Oriental Gold' is a cultivar of *Arundo formosana.*

Commercial classification: Oriental Gold Tiawan grass.

Parentage: Naturally occurring cane sport of *Arundo formosana.*

General description:

*Blooming habit.*—Blooms in late fall or in winter in response to short days.

*Plant habit.*—Herbaceous, clump-forming, ornamental grass with a fountain-like form and pendant foliage. Initial growth is un-branched until mature height is reached in late summer, branching at all cane nodes subsequently occurs to create a bushy habit.

*Height and spread.*—1.8 to 2 m (6 to 7 ft) in height with a spread of 1.8 to 2.7 m (6 to 9 ft) in 3 years when planted from a one gallon container. Moderate vigor.

*Hardiness.*—Zone 6 to 11.

*Culture.*—Coloration and Growth is best when grown in moist soil in full sun.

*Diseases and pests.*—No susceptibility or resistance to diseases or pests that affect *Arundo* has been observed.

*Root description.*—Short, knotty rhizomes with fibrous roots.

Growth and propagation:

*Propagation.*—Tissue culture and cane cuttings, canes from immature or mature shoots. 8 mm to 1.25 cm in diameter are stripped of foliage and allowed to float in aerated water kept at 75 to 80° F.

*Time required for root initiation.*—7 to 14 days to emerge and 21 to 28 days until cuttings can be taken.

*Time required for root development.*—Rooted cane cuttings will fully develop in a one quart container in 30 to 40 days when grown outdoors at night temperatures between 65 to 80° F. Night temperatures below 65° F. result in slower growth.

Culm (stem) description:

*General.*—Round, sheathed, pithy when young and hollow when mature.

*Culm color.*—144B on new growth, becoming woody in appearance when mature with color ranging from greyed-orange 164C to grey-brown 199C.

*Culm size.*—About 8 mm in diameter on young culms and secondary branches, mature canes reaching up to 1.25 cm in diameter and up to about 2 m in length.

*Stem surface.*—Glabrous.

*Internode length.*—About 0.5 to 2.0 cm on young growth and side branches, up to about 7 cm on mature canes.

*Ligule.*—Membranous area, surrounds leaf blade, 0.5 mm in height and 145d in color with very fine white hairs, not prominent.

*Branching.*—Multiple branches arise from rhizome then expand un-branched until mature height is reached, 3 to 5 branches then emerge from each node followed by secondary branching resulting in a witches broom effect.

Foliage description:

*Leaf shape.*—Linear, widest at base through the midpoint then narrowing to a point at apex.

*Leaf division.*—Simple.

*Leaf base.*—Sheathed.

*Leaf apex.*—Acute.

*Leaf aspect.*—Leaves are held at an angle of 30° to the culm, then Pendant, leaves are primarily flat or slightly involute.

*Leaf venation.*—Parallel, the midrib is raised on the lower surface, not prominent or conspicuous, color matches leaf color.

*Leaf margins.*—Entire, with sharp short bristles that are not visually noticeable.

*Leaf persistance.*—Dry to a tan color, 164D, but remain are persistent through winter.

*Leaf attachment.*—Sheathed. Leaf is sheathed from the base of culm and the leaf blade extends out from the culm at the ligule. Sheath entirely surrounds culm.

*Leaf size.*—0.4 to 1 cm at base and up to the midpoint, then tapering to a point at the apex, ranges from about 14 to 21 cm in length.

*Leaf number.*—Primary stems: about 20 to 30 until full height is reached and side branching occurs; side branches: typically about 8 to 15.

*Leaf arrangement.*—Alternate.

*Leaf surface.*—Glabrous on upper and lower surface with bristles on margins.

*Leaf color.*—Upper and lower leaves exhibit the same coloration, new leaves; base of yellow green 151A with greener stripes 144A and 141B (both present), mature leaves; base of yellow 1D with green stripes 137B, 139B, and 139C (typically all three green colored stripes are present). Stripes vary in width from 0.5 to 4 mm are cover about 50% of the leaf on both new and mature leaves.

Inflorescence description:

*General description.*—Feathery, airy panicle composed of numerous, slender racemes that emerge from the nodes of rachis in tufts. Racemes arch to one side, occasionally branch and are composed of single spikelets arranged in an alternate pattern. No reproductive organs were observed.

*Lastingness of inflorescence.*—Persistent.

*Fragrance.*—None.

*Panicle size.*—Approximately 35 cm in length and up to 2.5 cm in width.

*Panicle color.*—Emerge green (effectively 137D) tinted with purple on terminal spikelets (N77), changing to purple (effectively N77C) and maturing to a silvery purple due to the presence of numerous hairs (combintion of N77C and 155C).

*Rachis size.*—Up to about 30 cm in length, continuous with culm, 1 to 2 mm in diameter, branches emerging from rachis reach up to 14 cm in length and less than 1 mm in diameter.

*Rachis and rachilla color.*—137C.

*Raceme number.*—About 40 with 1 to 6 racemes emerging from each node.

*Spikelet description.*—One spikelet on a short rachilla arranged in an alternate pattern. Composed to two florets surrounded by a 2 glumes. Florets are enclosed by the a lemma and palea and the reproductive parts appears to be reduced.

*Spikelet rachilla.*—Very fine, about 2 to 4 mm in length, 137C in color.

*Spikelet bud.*—About 8 mm in length and 1 mm in width, 144D in color.

*Spikelet size.*—About 9 mm in length and 3 mm in width.

*Spikelet color.*—Lemma and palea N144D surrounded by glumes N77C.

*Glumes.*—Nearly equal in size, 6 to 8 mm in length and about 0.5 mm in width, lanceolate in shape, awnless, hyaline with shadings of purple (N77C).

*Lemma and palae.*—Appeared in both lower and upper floret, 4 mm in length, 0.5 mm in width, translucent in appearance and effectively N144D in color, numerous very fine hair-like bristles are present.

*Reproductive organs.*—Appeared reduced to leaf-like structures or not distinct enough to describe.

*Seed.*—No seed development has been observed.

It is claimed:

1. A new and distinct cultivar of *Arundo* plant named 'Oriental Gold' as herein illustrated and described.

* * * * *

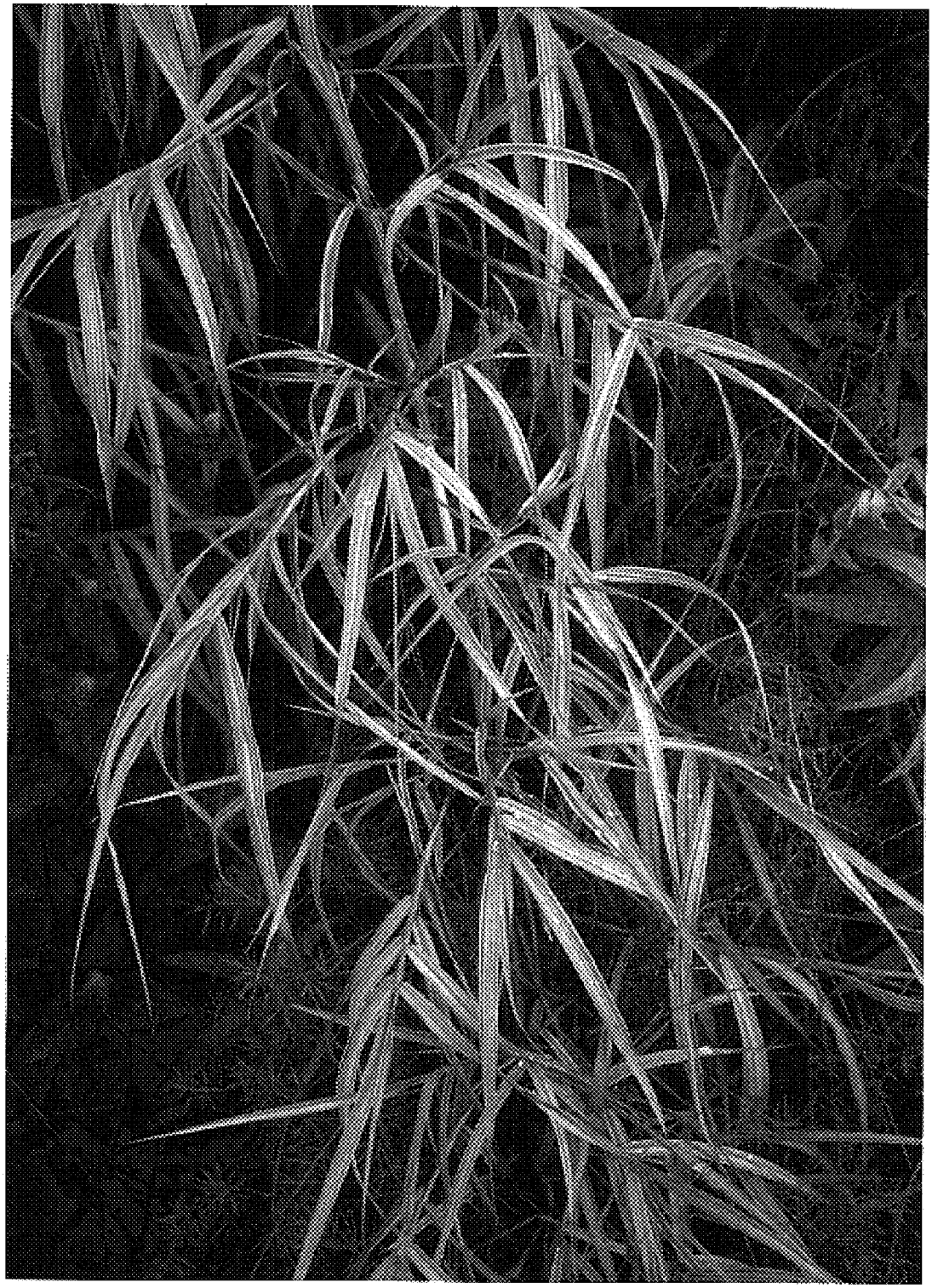
Figure One

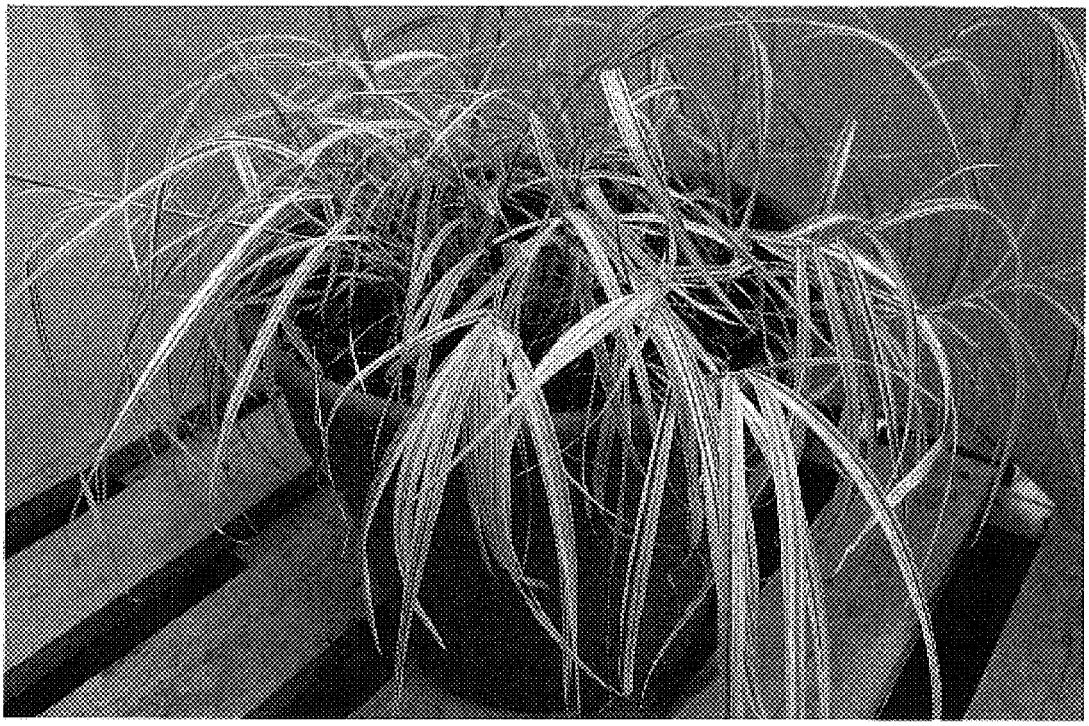
Figure Two
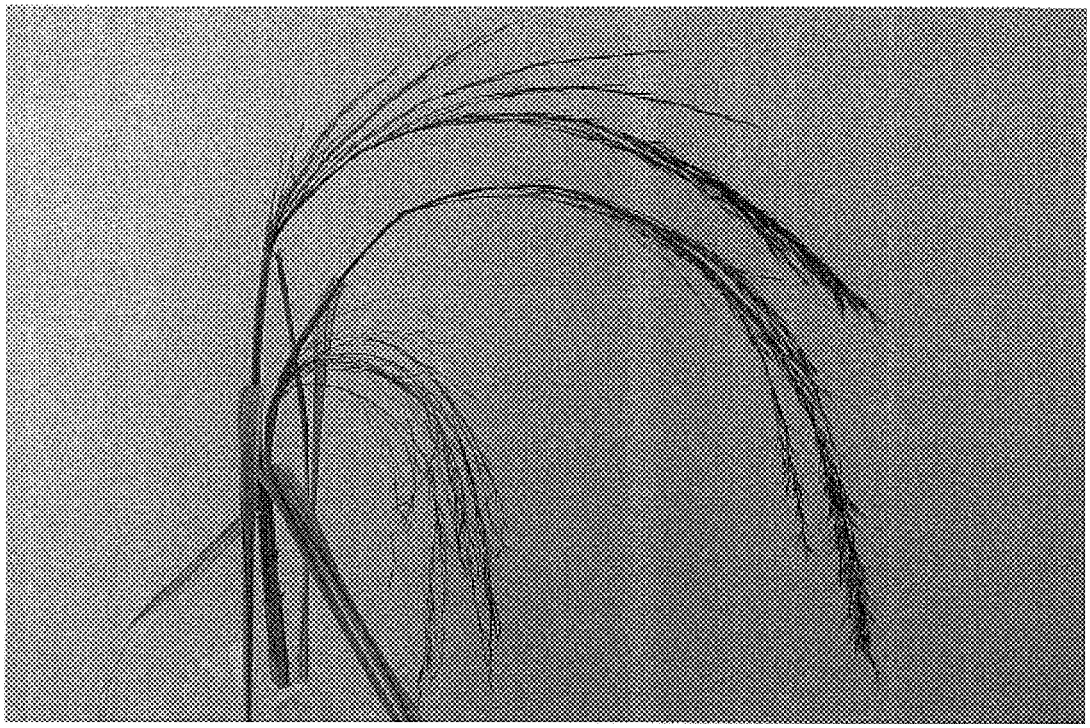
Figure Three